United States Patent
Ganagona et al.

(10) Patent No.: US 10,317,338 B2
(45) Date of Patent: Jun. 11, 2019

(54) METHOD AND ASSEMBLY FOR DETERMINING THE CARBON CONTENT IN SILICON

(71) Applicant: Infineon Technologies AG, Neubiberg (DE)

(72) Inventors: Naveen Goud Ganagona, Villach (AT); Moriz Jelinek, Villach (AT); Helmut Oefner, Zorneding (DE); Hans-Joachim Schulze, Taufkirchen (DE); Werner Schustereder, Villach (AT)

(73) Assignee: INFINEON TECHNOLOGIES AG, Neubiberg (DE)

( * ) Notice: Subject to any disclaimer, the term of this patent is extended or adjusted under 35 U.S.C. 154(b) by 0 days.

(21) Appl. No.: 15/716,598

(22) Filed: Sep. 27, 2017

(65) Prior Publication Data

US 2018/0088042 A1  Mar. 29, 2018

(30) Foreign Application Priority Data

Sep. 27, 2016  (DE) .......................... 10 2016 118 204

(51) Int. Cl.
*G01N 21/3563* (2014.01)
*G01N 21/35* (2014.01)

(52) U.S. Cl.
CPC . *G01N 21/3563* (2013.01); *G01N 2021/3568* (2013.01); *G01N 2021/3572* (2013.01); *G01N 2021/3595* (2013.01)

(58) Field of Classification Search
CPC ....... G01N 2021/3595; G01N 21/3563; G01N 2021/3568; G01N 2021/3572
See application file for complete search history.

(56) References Cited

U.S. PATENT DOCUMENTS

| 5,731,117 A * | 3/1998 | Ferrar .................... G03G 5/142 428/195.1 |
| 6,803,576 B2 | 10/2004 | Pretto et al. |
| 2015/0318159 A1* | 11/2015 | Badiei .................. H01J 49/105 250/282 |

FOREIGN PATENT DOCUMENTS

JP  2015156420 A  8/2015

OTHER PUBLICATIONS

M. Nakamura et al., "Photoluminescence Measurement of Carbon in Silicon Crystals Irradiated with High Energy Electrons", J. Electrochem. Soc., Dec. 1994, pp. 3576-3580, vol. 141, No. 12, The Electrochemical Society, Inc.
Naohisa Inoue et al., "Infrared measurement and irradiation of ultra low carbon concentration silicon crystal", Phys. Status Solidi C, 2012, pp. 1931-1936, vol. 9, No. 10-11, WILEY-VCH Verlag GmbH & Co. KGaA Weinheim.
(Continued)

*Primary Examiner* — David P Porta
(74) *Attorney, Agent, or Firm* — Viering, Jentschura & Partner mbB

(57) ABSTRACT

A method of determining the carbon content in a silicon sample may include: generating electrically active polyatomic complexes within the silicon sample. Each polyatomic complex may include at least one carbon atom. The method may further include: determining a quantity indicative of the content of the generated polyatomic complexes in the silicon sample, and determining the carbon content in the silicon sample from the determined quantity.

26 Claims, 5 Drawing Sheets

(56) References Cited

OTHER PUBLICATIONS

B. Langhanki et al., "Magnetic resonance studies of shallow donor centers in hydrogenated Cz—Si crystals", Physica B 302-303, 2001, pp. 212-219, Elsevier Science B. V.

C.P. Ewels et al., "Early stages of Oxygen Precipitation in Silicon", NATO ASI Series, 1996, pp. 141-162, vol. 17, 3. High Technology, Kluwer Academic Publishers, Dordrecht.

H. Ch. Alt et al., "Method to Determine Carbon in Silicon by Infrared Absorption Spectroscopy", Journal of The Electrochemical Society, 2003, pp. G498-G501, vol. 150, No. 8, The Electrochemical Society, Inc.

* cited by examiner

_US 10,317,338 B2_

METHOD AND ASSEMBLY FOR DETERMINING THE CARBON CONTENT IN SILICON

CROSS-REFERENCE TO RELATED APPLICATION

This application claims priority to German Patent Application Serial No. 10 2016 118 204.4, which was filed Sep. 27, 2016, and is incorporated herein by reference in its entirety.

TECHNICAL FIELD

Various embodiments relate generally to methods and measuring assemblies for determining the carbon content in a silicon sample.

BACKGROUND

To get a stable doping profile induced by proton irradiation one has to go for very oxygen lean floating zone (FZ) silicon material but at the cost of limited wafer diameter, since the production of floating zone silicon is not feasible for 300 mm diameter wafers and above which are required for various applications. Hence, there is a particular interest for silicon wafers with a diameter of 300 mm and more. Wafers with such large diameters can be manufactured from silicon ingots grown by the Chzochralski method, in particular by the magnetic Czochralski (MCz) method.

In MCz silicon, carbon and oxygen are the most abundant impurities. In the case of proton doping, the final doping concentration is critically affected by the presence of carbon atoms that are predominantly positioned in substitutional lattice sites.

In the following description, substitutional impurities, i.e., impurities located in substitutional lattice sites, will be labelled by a subscripted "S". Interstitial impurities will be labelled by a subscriped "I".

The carbon content in silicon is typically in the range of $5 \cdot 10^{14} - 1 \cdot 10^{16}$ cm$^{-3}$ which is enough to critically influence the proton-induced doping profiles. Therefore, an accurate measurement of the carbon content in this range is necessary in order to control the final proton-induced doping concentration.

Conventionally, the carbon content in silicon is determined by SIMS (Secondary Ion Mass Spectroscopy) or FTIR (Fourier Transform Infrared Spectroscopy). The utilization of these methods, however, is limited due to their rather high detection limits for carbon contents of about $3 \cdot 10^{15}$ cm$^{-3}$.

The sensitivity of FTIR is strongly impaired by the interference of the carbon ($C_S$) and silicon ($Si_S$) signals having nearly the same resonant frequencies or by the necessity of using reference samples with known low carbon contents which are not available as industry standards.

In addition, the conventional FTIR method can only detect substitutional carbon atoms $C_S$ located in regular lattice sites. Interstitial carbon atoms $C_I$ originating from other high temperature or irradiation process steps and possibly making up a substantial fraction of the carbon present in a silicon sample, however, are not detectable by this method. This also limits the sensitivity of the conventional FTIR method.

SUMMARY

According to one aspect of the present disclosure, a method of determining the carbon content in a silicon sample is provided. The method may include generating electrically active polyatomic complexes within the silicon substrate. Each polyatomic complex may include at least one carbon atom. The method may further include determining a quantity indicative of the content of the generated polyatomic complexes in the silicon sample, and determining the carbon content in the silicon sample from the determined quantity.

According to a second aspect of the present disclosure, a measuring assembly for determining the carbon content in a silicon sample is provided. The assembly may include a polyatomic-complex generation unit configured to generate electrically active polyatomic complexes within the silicon sample. Each polyatomic complex may include at least one carbon atom. The measuring assembly may further include a first determination unit configured to determine a quantity indicative of the content of the generated polyatomic complexes in the silicon sample, and a second determination unit configured to determine the carbon content in the silicon sample from the determined quantity.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1:
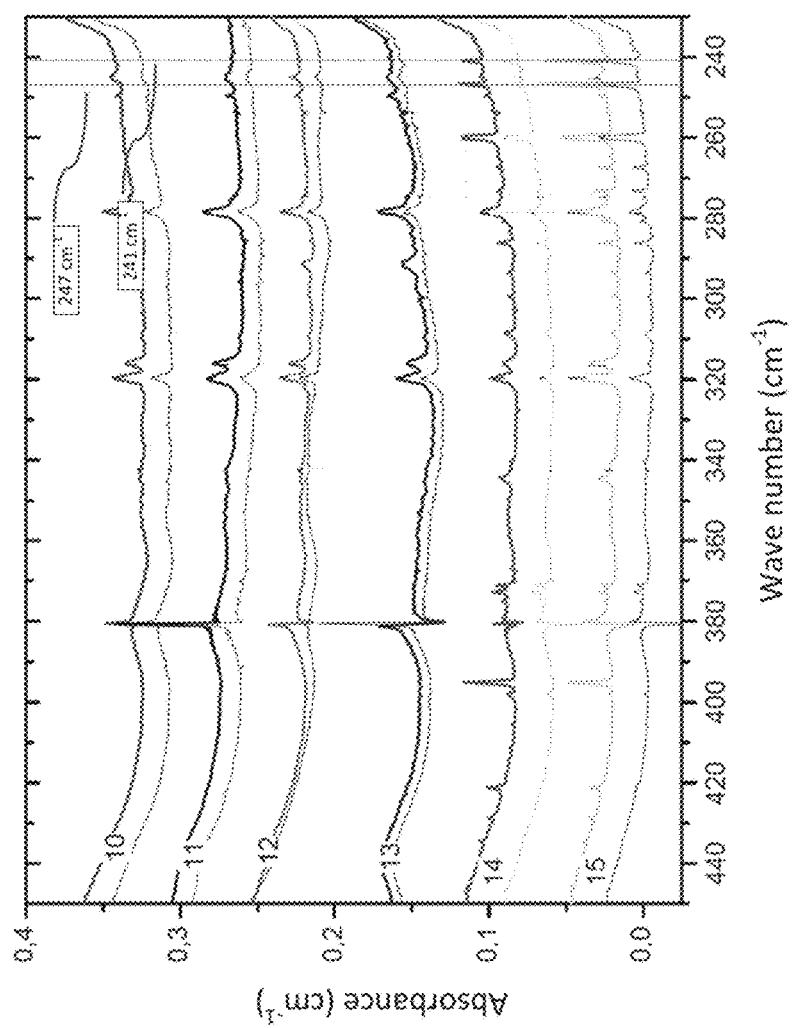
FIG. 1 shows low-temperature FTIR spectra of several silicon samples.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The shortcomings of the above-discussed conventional method of determining the carbon content in a silicon sample may be overcome by a method of determining the carbon content in a silicon sample that includes: generating electrically active polyatomic complexes within the silicon sample, determining a quantity indicative of the content of the generated polyatomic complexes in the silicon sample, and determining from the determined quantity the carbon content in the silicon sample. Each polyatomic complex may include at least one carbon atom.

By this method, the carbon content is determined indirectly by determining a quantity indicative of the content of polyatomic complexes including at least one carbon atom, instead of detecting signals directly originating from substitutional carbon atoms $C_S$. Therefore, the above-discussed overlap of signals originating from $Si_S$ and $C_S$ is irrelevant for the inventive method and does not limit the achievable sensitivity. In this way, the sensitivity can be improved by nearly one order of magnitude as compared to the above-discussed conventional method to about $5 \cdot 10^{14}$ $cm^{-3}$.

Prior to forming the polyatomic complexes, a substantial part of the carbon atoms present in the silicon sample is found in substitutional lattice sites. As indicated in equation (1) below, generating the polyatomic complexes may include displacing carbon atoms from the substitutional lattice sites to interstitial lattice sites. This may be performed by particle irradiation of the silicon sample, in particular with protons and/or electrons and/or neutrons and/or alpha particles.

$$Si_I + C_S \rightarrow C_I + Si_S \quad (1)$$

At room temperature (RT), interstitial carbon is unstable due to diffusion leading to trapping of migrating interstitial carbon atoms by interstitial oxygen atoms $O_I$, thereby forming interstitial $C_IO_I$ complexes, as indicated in equation (2).

$$C_I + O_I \rightarrow C_IO_I \quad (2)$$

The interstitial complexes $C_IO_I$ are stable up to 350° C. According to an aspect of the present invention, a higher thermal stability may be achieved by interstitial polyatomic complexes that, besides carbon, also include at least one hydrogen atom $H_m$ and/or a plurality of interstitial oxygen atoms $O_{nI}$. Here, n, m are integer numbers denoting the number of interstitial oxygen atoms $O_I$ and hydrogen atoms H, respectively, that are present in an individual interstitial polyatomic complex. Such interstitial polyatomic complexes may, hence, include at least one hydrogen atom H introduced by the particle irradiation, and a plurality of interstitial oxygen atoms $O_{nI}$. In the following, these interstitial polyatomic complexes are denoted by $C_IO_{nI}$—$H_m$.

These complexes are thermally stable up to temperatures of above 450° C. In an exemplary embodiment, at least some or even most of the interstitial polyatomic complexes include a plurality of interstitial oxygen atoms $O_I$ and/or at least one hydrogen atom H. The generation efficiency of these interstitial complexes $C_IO_{nI}$—$H_m$ can be increased by annealing the silicon sample after the irradiation thereof with particles.

The annealing may be performed at a temperature in a range from about 450° C. to about 520° C. In an exemplary embodiment, the annealing may be performed at a temperature of about 490° C.

The annealing may be performed over a period in a range from about 30 minutes to about 7 hours. In an exemplary embodiment, the annealing may be performed over a period in a range of 1 to about 5 hours.

The above-discussed interstitial polyatomic complexes may act as hydrogen-induced shallow thermal donors (STD-H). This means that these polyatomic complexes can generate energy states in the band gap of silicon close to the conduction band. The gap between these energy states and the conduction band is less than the thermal energy at room temperature.

In the far-infrared (FIR) range, silicon samples including $C_IO_{nI}$—$H_m$ complexes show clear absorption peaks at 241 $cm^{-1}$ and 247 $cm^{-1}$ that are assigned to these complexes.

The determination of the quantity indicative of the content of the polyatomic complexes in the silicon sample may be performed by a spectroscopic method, in particular by Fourier Transform Infrared Spectroscopy (FTIR).

FTIR is a spectroscopic method of determining the ability of a sample to absorb electromagnetic radiation of a given wavelength in the infrared regime which is indicative of the individual composition of the sample to be analyzed. FTIR involves the irradiation of the sample with an infrared light beam of a predetermined wavelength range. During the irradiation of the sample, the absorption of the sample is measured. This gives a first data point. Subsequently, the wavelength range of the light beam is modified a plurality of times and the absorption characteristics of the sample are measured for each light beam, giving a plurality of corresponding data points. Afterwards, the light absorption for each wavelength is calculated by Fourier transformation. The spectrum obtained in this way includes a plurality of characteristic peaks related to the individual components of the analyzed sample. In this way, the above-mentioned peaks at 241 $cm^{-1}$ and 247 $cm^{-1}$ can be detected.

As the quantity indicative of the content of the interstitial polyatomic complexes, the respective peak heights and/or the integrated areas of the peaks can be determined. Since in this case a plurality of characteristic peaks is present, the sum of the integrated areas of the peaks can also be determined as the quantity indicative of the content of the polyatomic complexes.

The resolution of the peaks may be increased by reducing the temperature of the sample to be analyzed. FTIR performed at low temperatures is referred to as Low-Temperature FTIR (LT FTIR). The spectrum acquisition may be performed at a temperature in a range of about 4 to 20 K. In an exemplary embodiment, the temperature may be about 10 K. Such low temperatures may be provided by liquid helium having a temperature of about 4 K. Starting from this base temperature, the temperature of the sample may be increased to a higher temperature in the above range by Joule heating.

In case the polyatomic complexes act as donors, the sample may be illuminated with visible light with a power of, e.g., 100 W during the acquisition of the FTIR spectrum in order to suppress or even eliminate the compensation of the donors due to acceptors present in the silicon sample. In this way, the content of the polyatomic complexes can be more accurately determined.

LT FTIR spectra of differently processed silicon samples are shown in FIG. 1. FIG. 1 includes a total of twelve spectra grouped into six groups labelled "10", "11", "12", "13", "14", and "15", respectively. The respective two spectra of an individual group have been acquired from the same silicon sample, however, under different illumination conditions. More specifically, the respective upper spectrum of a given group has been acquired from an illuminated silicon sample, and the respective lower spectrum of a given group has been acquired in a dark environment, i.e. the respective sample was not illuminated during the spectrum acquisition.

The details of the groups of spectra shown in FIG. 1 are:
10: low carbon content, not irradiated with particles, not annealed,
11: high carbon content, not irradiated with particles, not annealed,
12: low carbon content, irradiated with protons, not annealed,
13: high carbon content, irradiated with protons, not annealed,
14: low carbon content, irradiated with protons and annealed,
15: high carbon content, irradiated with protons and annealed.

Here, a low carbon content refers to a carbon content of about $1 \cdot 10^{15}$ cm$^{-3}$, and a high carbon content refers to a carbon content of about $3.3 \cdot 10^{15}$ cm$^{-3}$.

Figure 2:
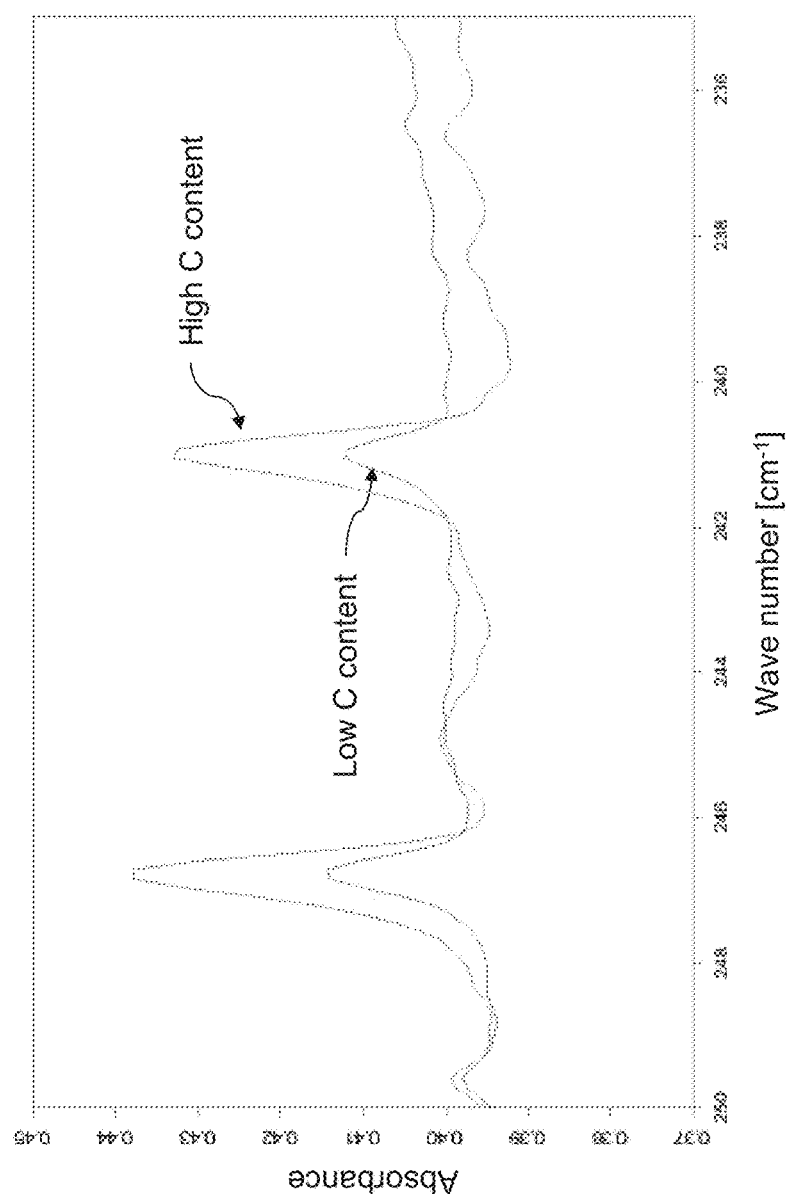
FIG. 2 shows an enlarged view of characteristic peaks at 241 cm$^{-1}$ and 247 cm$^{-1}$ of two FTIR spectra shown in FIG. 1.

The characteristic peaks at 241 cm$^{-1}$ and at 247 cm$^{-1}$ assigned to the polyatomic complexes $C_iO_{nI}$—$H_m$ are indicated by the vertical lines in FIG. 1. As can clearly be seen in FIG. 1, only the spectra of groups "14" and "15" show characteristic absorption peaks at 241 cm$^{-1}$ and at 247 cm$^{-1}$. In addition, the heights and areas of the characteristic peaks are correlated with the carbon contents of the individual silicon samples, i.e. the heights and areas of the characteristic peaks increase with increasing carbon content. This correlation is more clearly shown in FIG. 2 in which only the characteristic peaks at 241 cm$^{-1}$ and at 247 cm$^{-1}$ of the respective upper FTIR spectra of groups "14" and "15" are shown. Here, the baselines of the spectra have been aligned to more clearly show the different heights of the characteristic peaks associated with different carbon contents.

As previously discussed, as a quantity indicative of the content of the complexes $C_iO_{nI}$—$H_m$ in the silicon sample, the sum of the areas of these characteristic peaks may be determined.

From the sum of the areas of these characteristic peaks, a corresponding carbon content can be derived using a calibration curve that assigns a unique carbon content to the determined sum of peak areas.

A calibration curve may be determined in advance using a plurality of silicon samples with known carbon contents, measured, e.g., by another LT-FTIR method (see, e.g., H. Ch. Alt, et al., Journal of The Electrochemical Society, 150 (8) G498-G501 (2003)). These samples may be subjected to the above discussed method of generating the polyatomic complexes, i.e., particle irradiation and annealing. Afterwards, the absorption characteristics of the respective samples may be determined by LT FTIR providing respective peak areas that can be assigned to the known carbon contents.

Figure 3:
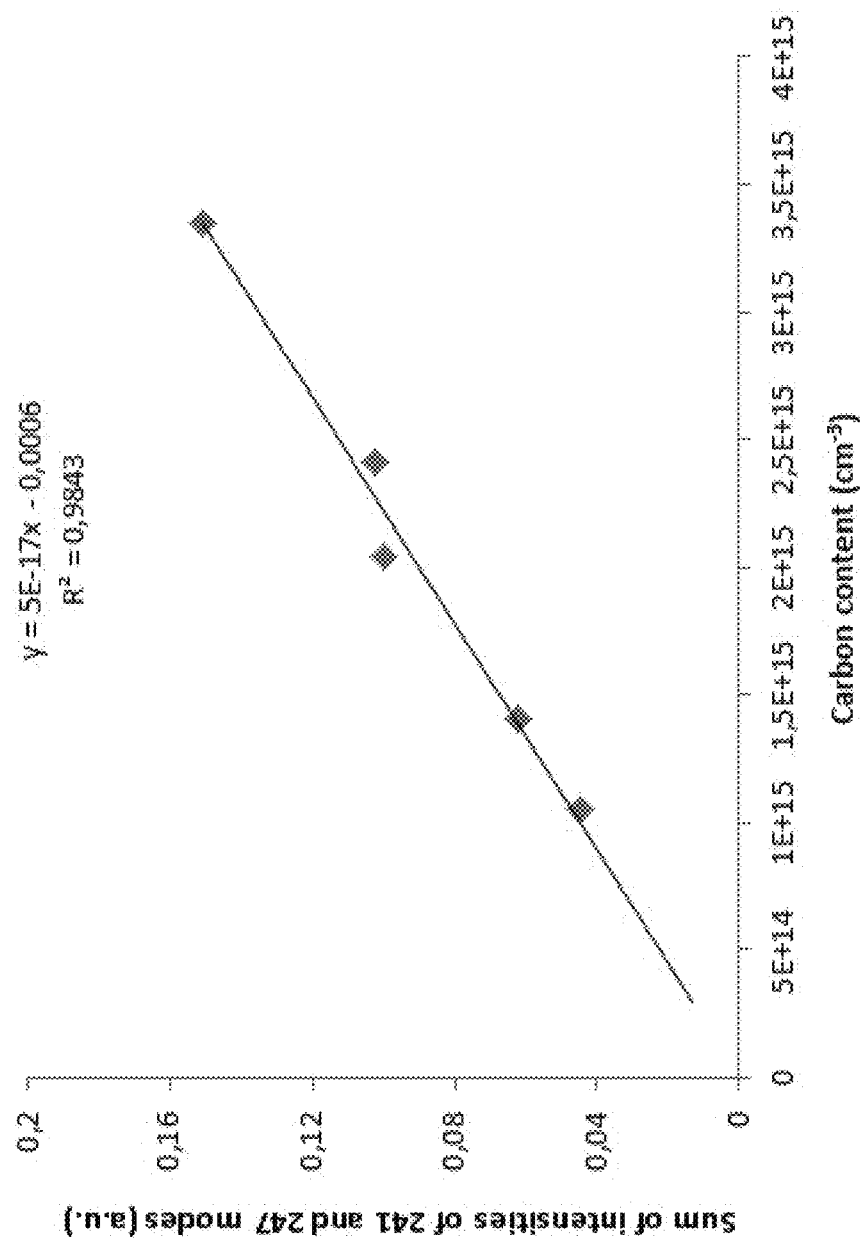
FIG. 3 shows the dependence of the sum of intensities of characteristic peaks of polyatomic complexes in a silicon sample at 241 cm$^{-1}$ and 247 cm$^{-1}$ on the carbon content in the silicon sample.

The relationship between the sum of the characteristic peaks of the above-discussed $C_iO_{nI}$—$H_m$ complexes and the corresponding carbon contents is shown in FIG. 3. By fitting a fit function to this data values, a calibration curve can be derived.

In FIG. 3, a linear function of the general form y=mx+t has been fitted to the measured data points yielding a value of $5 \cdot 10^{14}$ for m, and −0.0006 for t. The assumed linear relationship between the sum of the peak areas and the carbon content is confirmed by a $R^2$ value of 0.9843 which is indicative of a high goodness of fit.

The fit function can be used to assign a measured sum of peak areas to a corresponding carbon content. This also allows an extrapolation down to low carbon contents for which no industry standards, i.e., samples with a known carbon content, are available. The error related to such an extrapolation is negligible due to the high goodness of fit.

The determined quantity indicative of the carbon content such as the heights and integrated areas of characteristic peaks obtained by FTIR may also depend on the oxygen content of the sample to be analyzed.

The oxygen content may be considered by a respective calibration curve. In an exemplary embodiment, a plurality of sets of standards with known carbon contents and a known fixed oxygen content for each set can be used to derive a plurality of calibration curves for different oxygen contents. The concentration of oxygen in silicon can be easily and very precisely measured by FTIR at room temperature (RT FTIR).

In practice, the oxygen content in silicon can be precisely adjusted. Therefore, for a given application, large variations of the oxygen contents between different samples can be avoided. Consequently, the influence of variations of the oxygen content on the accuracy of the determination of the carbon content according to the present method can be basically ignored.

Figure 4:
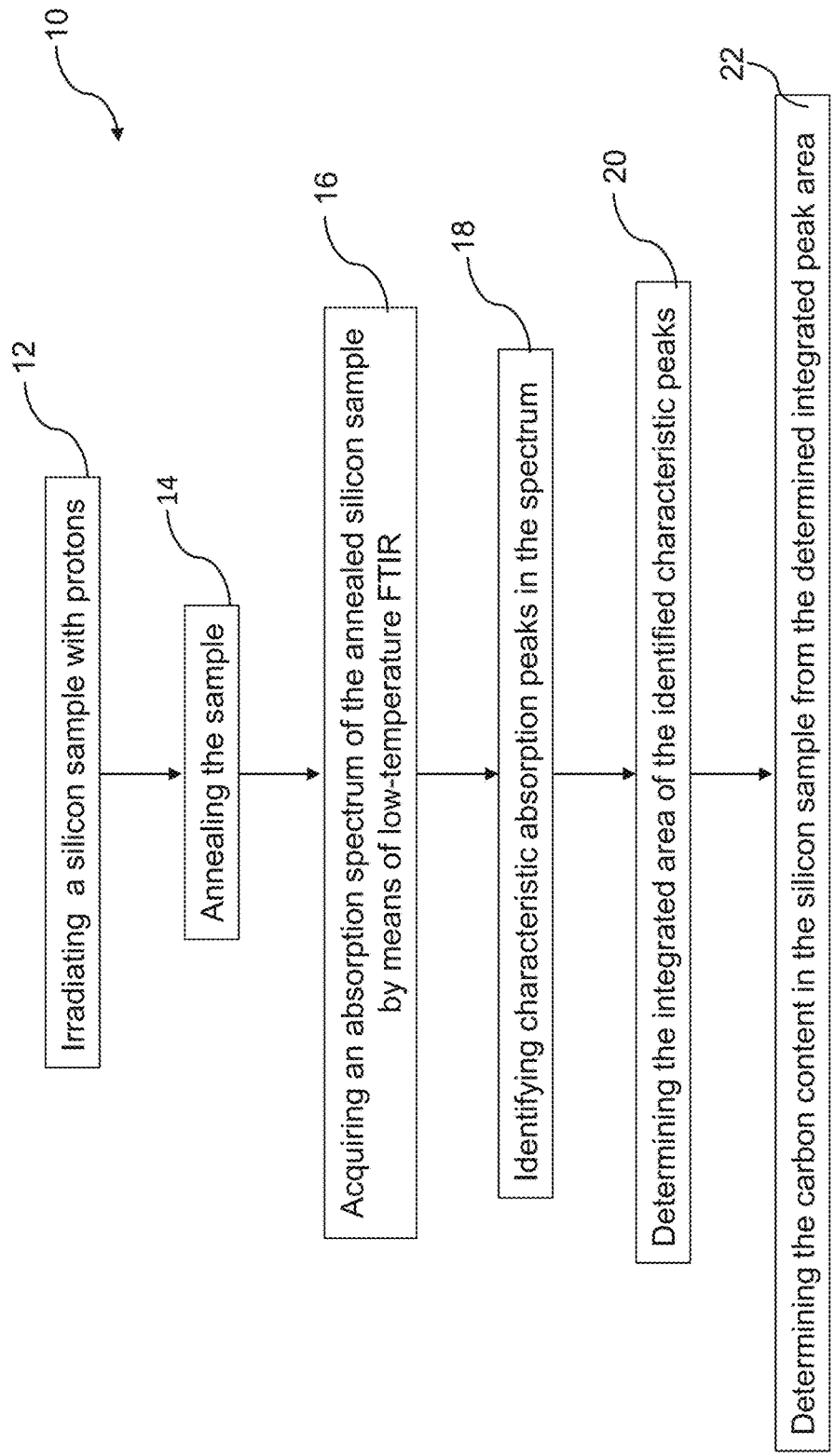
FIG. 4 shows a flow chart of an exemplary method of determining the carbon content in a silicon sample.

A flow chart of an exemplary method 10 of detecting the carbon content in a silicon sample summarizing the above is depicted in FIG. 4.

Method 10 may include:
irradiating a silicon sample with protons (12),
annealing the sample (14),
acquiring an absorption spectrum of the annealed silicon sample by means of low-temperature FTIR (16),
identifying characteristic absorption peaks in the spectrum (18),
determining the integrated area of the identified characteristic peaks (20), and
determining the carbon content in the silicon sample from the determined integrated peak area (22).

The above described methods may be applied in particular to Czochralski silicon samples due to their higher oxygen content as compared to float-zone silicon. A high oxygen content may be beneficial for the generation of a large number of the above-described polyatomic complexes that include interstitial oxygen atoms as trapping sites for carbon atoms.

In the Czochralski method, polycrystalline silicon fragments are molten inside a silica crucible. Silicon single crystals are grown by slowly pulling a crystal seed up from the molten silicon. In this way, an ingot is grown from which wafers can be cut in subsequent process steps.

In an exemplary embodiment, the silicon sample may be grown by the magnetic Czochralski (MCz) method. This method is similar to the conventional Czochralski method, except that the ingot is grown in a strong magnetic field which is used to dampen oscillations in the silicon melt. More specifically, in the magnetic Czochralski method, the Lorentz force resulting from the applied magnetic field influences the flow of molten silicon in the crucible and reduces the amplitude of the melt fluctuations. In this way, the oxygen concentration can be better controlled.

A schematic drawing of a measuring assembly 100 for determining the carbon content in a silicon sample 102 according to the method described above is shown in FIG. 5. The above explanations with respect to the method apply also to measuring assembly 100.

Figure 5:
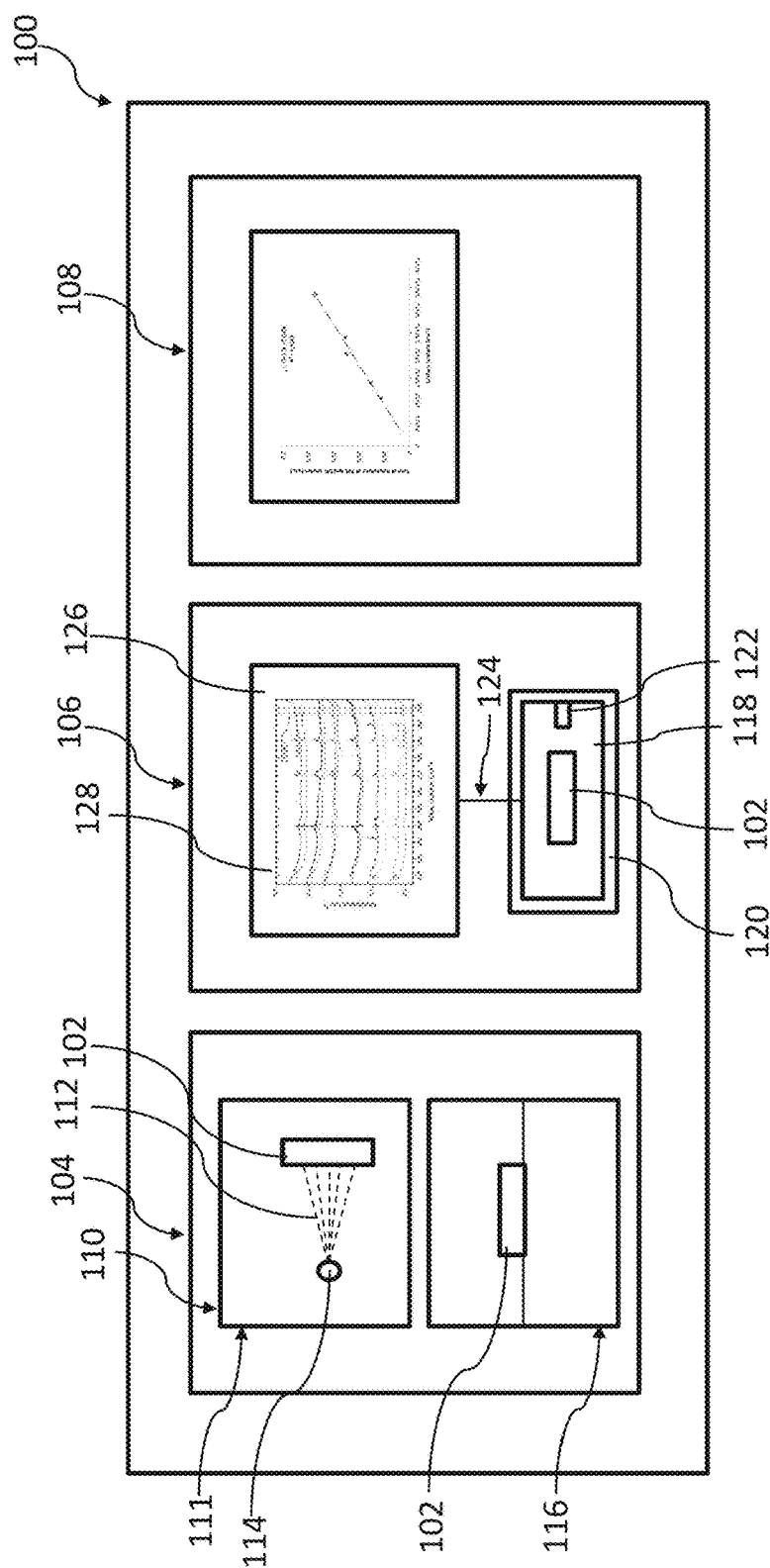
FIG. 5 shows a schematic view of a measuring assembly for determining the carbon content in a silicon sample.

As shown in FIG. 5, the measuring assembly 100 may include a polyatomic-complex generation unit 104 configured to generate the electrically active polyatomic complexes within the silicon sample 102, a first determination unit 106 configured to determine the quantity indicative of the content of the generated polyatomic complexes in the silicon sample 102, and a second determination unit 108 configured to determine the carbon content in the silicon sample 102 from the determined quantity.

The polyatomic-complex generation unit 100 may include an irradiation sub-unit 111 configured to irradiate the silicon sample 102 with particles 112 such as protons and/or electrons and/or neutrons and/or alpha particles. As indicated in FIG. 5, the irradiation sub-unit 111 may include a particle source 114 such as a hydrogen cell emitting protons 112 that may be accelerated towards the silicon sample 102 by an electric field.

The polyatomic-complex generation unit 104 may further include an annealing sub-unit 116 configured to anneal the silicon sample 102 at temperatures of several hundreds of degrees Kelvin, as discussed above with respect to the method.

The first determination unit 106 may include a spectrometer 118 for determining the quantity indicative of the content of the polyatomic complexes in the silicon sample 102. The spectrometer 118 may be configured as an FTIR spectrometer. As also discussed above, the resolution of the FTIR spectrometer can be improved by operating the spectrometer 118 at low temperatures such as in a range from about 4 K to about 20 K. Such low temperatures may be provided by a liquid He cryostat 120 configured to house the FTIR spectrometer 118.

The first determination unit 106 may include lighting means 122 configured to irradiate the silicon sample 102 in the spectrometer 118 with visible light in order to reduce the compensation effect of acceptors present in the silicon sample 102 on the polyatomic complexes that may act as shallow thermal donors. The lighting means 122 may be configured as an LED. The lighting means 122 may be operated at the low temperatures of the cryostat 120, as indicated in FIG. 5. Alternatively, the lighting means 122 may be operated at room temperature and the light output by the lighting means 122 may be introduced into the cryostat by an optical fiber.

The signals acquired by the spectrometer 118 may be transmitted via data lines 124 to a processing unit 126 such as to a computer. The processing unit 126 may be equipped with suitable software to generate a spectrum 128 from the data received from the spectrometer 118.

The processing unit 126 may also be configured to determine at least one characteristic peak originating from the polyatomic complexes in the spectrum 128, and to determine as the quantity indicative of the content of the polyatomic complexes in the silicon sample 102 the height of the at least one identified characteristic peak and/or the area under the at least one identified characteristic peak.

In an exemplary embodiment, the processing unit 126 may be configured to identify a plurality of characteristic peaks originating from the interstitial polyatomic complexes, and to determine the quantity indicative of the content of the polyatomic complexes in the silicon sample 102 as the sum of the areas under the plurality of characteristic peaks.

The second determination unit 108 may be configured to determine the carbon content in the silicon sample 102 using a calibration curve assigning a unique carbon content to the determined quantity indicative of the content of the polyatomic complexes in the silicon sample 102.

Since the determination of the carbon content in the silicon sample 102 may be influenced by the oxygen content in the silicon sample 102, the second determination unit 108 may be configured to choose the calibration curve depending on the oxygen content in the silicon sample 102.

It is to be noted that even though the first determination unit 106 and the second determination unit 108 have been described as two different units, a measuring assembly is conceivable that includes a unit configured both to determine the quantity indicative of the content of the polyatomic complexes and to determine the carbon content from the determined quantity. Such a unit may be configured as a computer equipped with an appropriate software to accomplish these tasks from the signals input from the spectrometer 118.

In the following, various aspects of the present disclosure will be illustrated:

Example 1 is a method of determining the carbon content in a silicon sample. The method may include: generating electrically active polyatomic complexes within the silicon sample. Each polyatomic complex may include at least one carbon atom. The method may further include determining a quantity indicative of the content of the generated polyatomic complexes in the silicon sample, and determining the carbon content in the silicon sample from the determined quantity.

In Example 2, the subject matter of Example 1 can optionally further include that at least one polyatomic complex, a plurality of polyatomic complexes, or most polyatomic complexes includes/include at least one oxygen atom or a plurality of oxygen atoms.

In Example 3, the subject matter of any one of Examples 1 or 2 can optionally further include that the generating the polyatomic complexes includes displacing carbon atoms from substitutional lattice sites to interstitial lattice sites.

In Example 4, the subject matter of Example 3 can optionally further include that the displacing is performed by particle irradiation of the silicon sample.

In Example 5, the subject matter of Example 4 can optionally further include that the particles include protons and/or electrons and/or neutrons and/or alpha particles.

In Example 6, the subject matter of any one of Examples 1 to 5 can optionally further include that the generating the polyatomic complexes includes annealing the silicon sample.

In Example 7, the subject matter of Example 6 can optionally further include that the annealing is performed at a temperature in a range from about 450° C. to about 520° C.

In Example 8, the subject matter of Example 7 can optionally further include that the annealing is performed at a temperature of about 490° C.

In Example 9, the subject matter of any one of Examples 6 to 8 can optionally further include that the annealing is performed over a period in a range from about 30 minutes to about 7 hours.

In Example 10, the subject matter of Example 9 can optionally further include that the annealing is performed over a period of about 1 to 5 hours.

In Example 11, the subject matter of any one of Examples 1 to 10 can optionally further include that at least some of the polyatomic complexes include at least one hydrogen atom.

In Example 12, the subject matter of any one of Examples 1 to 11 can optionally further include that at least some of the polyatomic complexes are configured as shallow donors.

In Example 13, the subject matter of any one of Examples 1 to 12 can optionally further include that the determining the quantity indicative of the content of the polyatomic complexes in the silicon sample is performed by a spectroscopic method.

In Example 14, the subject matter of Example 13 can optionally further include that the spectroscopic method includes Fourier Transform Infrared Spectroscopy (FTIR).

In Example 15, the subject matter of Example 14 can optionally further include that the Fourier Transform Infrared Spectroscopy (FTIR) is performed at a temperature in a range from about 4 K to about 20 K.

In Example 16, the subject matter of Example 15 can optionally further include that the Fourier Transform Infrared Spectroscopy (FTIR) is performed at a temperature of about 10 K.

In Example 17, the subject matter of any one of Examples 13 to 16 can optionally further include that during the determining the quantity indicative of the content of the polyatomic complexes, the silicon sample is irradiated with visible light.

In Example 18, the subject matter of any one of Examples 13 to 17 can optionally further include: identifying at least one characteristic peak in a spectrum obtained by the spectroscopic method.

In Example 19, the subject matter of Example 18 can optionally further include that the quantity indicative of the content of the polyatomic complexes in the silicon sample is determined as the height of the identified at least one characteristic peak and/or the integrated area of the identified at least one characteristic peak.

In Example 20, the subject matter of Examples 18 and 19 can optionally further include that the spectroscopic method includes the identification of a plurality of characteristic peaks and the quantity indicative of the content of the polyatomic complexes in the silicon sample is determined as the sum of the integrated areas under the plurality of characteristic peaks.

In Example 21, the subject matter of any one of Examples 1 to 20 can optionally further include that the determining the carbon content in the silicon sample is performed using a calibration curve assigning a unique carbon content to the determined quantity indicative of the content of the polyatomic complexes in the silicon sample.

In Examples 22, the subject matter of Example 21 can optionally further include that the calibration curve is chosen depending on the oxygen content in the silicon sample to be analyzed.

In Example 23, the subject matter of Example 22 can optionally further include that the oxygen content in the silicon sample to be analyzed is determined by Fourier Transform Infrared Spectroscopy (FTIR).

In Example 24, the subject matter of Example 22 can optionally further include that the oxygen content is determined by Fourier Transform Infrared Spectroscopy (FTIR) performed at room temperature.

In Example 25, the subject matter of any one of Examples 1 to 24 can optionally further include that the silicon sample is grown by the Czochralski method.

In Example 26, the subject matter of Example 25 can optionally further include that the silicon sample is grown by the magnetic Czochralski method.

Example 27 is a measuring assembly for determining the carbon content in a silicon sample. The assembly may include: a polyatomic-complex generation unit configured to generate electrically active polyatomic complexes within the silicon sample. Each polyatomic complex may include at least one carbon atom. The measuring assembly may further include a first determination unit configured to determine a quantity indicative of the content of the generated polyatomic complexes in the silicon sample, and a second determination unit configured to determine the carbon content in the silicon sample from the determined quantity.

In Example 28, the subject matter of Example 27 can optionally further include that at least one polyatomic complex, a plurality of polyatomic complexes, or most polyatomic complexes includes/include at least one oxygen atom or a plurality of oxygen atoms.

In Example 29, the subject matter of any one of Examples 27 or 28 can optionally further include that the polyatomic complex generation unit includes an irradiation sub-unit configured to irradiate the silicon sample with particles.

In Example 30, the subject matter of Example 29 can optionally further include that the particles include protons and/or electrons and/or neutrons and/or alpha particles.

In Example 31, the subject matter of any one of Examples 27 to 30 can optionally further include that the polyatomic-complex generation unit includes an annealing sub-unit configured to anneal the silicon sample.

In Example 32, the subject matter of any one of Examples 27 to 31 can optionally further include that the first determination unit includes a spectrometer.

In Example 33, the subject matter of Example 32 can optionally further include that the spectrometer is configured as an FTIR spectrometer.

In Example 34, the subject matter of any one of Examples 32 or 33 can optionally further include that the spectrometer is operable at a temperature in a range from about 4 K to about 20 K.

In Example 35, the subject matter of any one of Examples 27 to 34 can optionally further include that the first determination unit is configured to irradiate the silicon sample with visible light during determining the quantity indicative of the content of the polyatomic complexes.

In Example 36, the subject matter of any one of Examples 32 to 35 can optionally further include that the first determination unit is configured to determine at least one characteristic peak in a spectrum acquired by means of the spectrometer.

In Example 37, the subject matter of Example 36 can optionally further include that the first determination unit is configured to determine the height of the at least one characteristic peak and/or the area under the at least one characteristic peak as the quantity indicative of the content of the polyatomic complexes in the silicon sample.

In Example 38, the subject matter of Examples 36 and 37 can optionally further include that the first determination unit is configured to identify a plurality of characteristic peaks and to determine the quantity indicative of the content of the polyatomic complexes in the silicon sample as the sum of the areas under the plurality of characteristic peaks.

In Example 39, the subject matter of any one of Examples 27 to 38 can optionally further include that the second determination unit is configured to determine the carbon content in the silicon sample using a calibration curve assigning a unique carbon content to the determined quantity indicative of the content of the polyatomic complexes in the silicon sample.

In Example 40, the subject matter of Example 39 can optionally further include that the the second determination unit is configured to choose the calibration curve depending on the oxygen content in the silicon sample to be analyzed.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of determining a carbon content in a silicon sample, the method comprising:
    generating electrically active polyatomic complexes within the silicon sample, wherein each polyatomic complex comprises at least one carbon atom;
    determining a quantity indicative of the content of the generated polyatomic complexes in the silicon sample; and
    determining the carbon content in the silicon sample from the determined quantity.

2. The method of claim 1,
wherein at least one polyatomic complex, a plurality of polyatomic complexes, or most polyatomic complexes comprises/comprise at least one oxygen atom or a plurality of oxygen atoms.

3. The method of claim 1,
wherein the generating the polyatomic complexes comprises displacing carbon atoms from substitutional lattice sites to interstitial lattice sites,
wherein optionally the displacing is performed by particle irradiation of the silicon sample,
wherein further optionally the particles comprise protons and/or electrons and/or neutrons and/or alpha particles.

4. The method of claim 1,
wherein the generating the polyatomic complexes comprises annealing the silicon sample,
wherein optionally the annealing is performed at a temperature in a range from about 450° C. to about 520° C., further optionally at a temperature of about 490° C.

5. The method of claim 4,
wherein the annealing is performed over a period in a range from about 30 minutes to about 7 hours, optionally over a period in a range from about 1 hour to about 5 hours.

6. The method of claim 1,
wherein at least some of the polyatomic complexes comprise at least one hydrogen atom.

7. The method of claim 1,
wherein at least some of the polyatomic complexes are configured as shallow donors.

8. The method of claim 1,
wherein the determining the quantity indicative of the content of the polyatomic complexes in the silicon sample is performed by a spectroscopic method,
wherein optionally the spectroscopic method comprises Fourier Transform Infrared Spectroscopy (FTIR),
wherein further optionally the Fourier Transform Infrared Spectroscopy (FTIR) is performed at a temperature in a range from about 4 K to about 20 K, further optionally at a temperature of about 10 K.

9. The method of claim 8,
wherein during the determination of the quantity indicative of the content of the polyatomic complexes, the silicon sample is irradiated with visible light.

10. The method of claim 8, further comprising:
identifying at least one characteristic peak in a spectrum obtained by the spectroscopic method.

11. The method of claim 10,
wherein the quantity indicative of the content of the polyatomic complexes in the silicon sample is determined as a height of the identified at least one characteristic peak and/or an integrated area of the identified at least one characteristic peak.

12. The method of claim 11,
wherein the spectroscopic method comprises the identification of a plurality of characteristic peaks and the quantity indicative of the content of the polyatomic complexes in the silicon sample is determined as a sum of the integrated areas of the plurality of characteristic peaks.

13. The method of claim 1,
wherein the determining the carbon content in the silicon sample is performed using a calibration curve assigning a unique carbon content to the determined quantity indicative of the content of the polyatomic complexes in the silicon sample.

14. The method of claim 13,
wherein the calibration curve is chosen depending on an oxygen content in the silicon sample to be analyzed,
wherein optionally the oxygen content in the silicon sample to be analyzed is determined by Fourier Transform Infrared Spectroscopy (FTIR),
wherein further optionally the oxygen content is determined by Fourier Transform Infrared Spectroscopy (FTIR) performed at room temperature.

15. The method of claim 1,
wherein the silicon sample is grown by the Czochralski method, optionally by the magnetic Czochralski method.

16. A measuring assembly for determining the carbon content in a silicon sample, wherein the assembly comprises:
a polyatomic-complex generation unit configured to generate electrically active polyatomic complexes within the silicon sample, wherein each polyatomic complex comprises at least one carbon atom;
a first determination unit configured to determine a quantity indicative of the content of the generated polyatomic complexes in the silicon sample; and
a second determination unit configured to determine the carbon content in the silicon sample from the determined quantity.

17. The measuring assembly of claim 16,
wherein at least one polyatomic complex, a plurality of polyatomic complexes, or most polyatomic complexes comprises/comprise at least one oxygen atom or a plurality of oxygen atoms.

18. The measuring assembly of claim 16,
wherein the polyatomic complex generation unit comprises an irradiation sub-unit configured to irradiate the silicon sample with particles, wherein optionally the particles comprise protons and/or electrons and/or neutrons and/or alpha particles.

19. The measuring assembly of claim 16,
wherein the polyatomic-complex generation unit comprises an annealing sub-unit configured to anneal the silicon sample.

20. The measuring assembly of claim 16,
wherein the first determination unit includes a spectrometer, optionally configured as an FTIR spectrometer.

21. The measuring assembly of claim 20,
wherein the spectrometer is operable at a temperature in a range from about 4 K to about 20 K.

22. The measuring assembly of claim 20,
wherein the first determination unit is configured to determine at least one characteristic peak in a spectrum acquired by means of the spectrometer.

23. The measuring assembly of claim 22,
wherein the first determination unit is configured to determine a height of the at least one characteristic peak and/or an area under the at least one characteristic peak as the quantity indicative of the content of the polyatomic complexes in the silicon sample.

24. The measuring assembly of claim 23,
wherein the first determination unit is configured to identify a plurality of characteristic peaks and to determine the quantity indicative of the content of the polyatomic complexes in the silicon sample as a sum of the areas under the plurality of characteristic peaks.

25. The measuring assembly of claim 16,
wherein the first determination unit is configured to irradiate the silicon sample with visible light during determining the quantity indicative of the content of the polyatomic complexes.

26. The measuring assembly of claim 16,
wherein the second determination unit is configured to determine the carbon content in the silicon sample using a calibration curve assigning a unique carbon content to the determined quantity indicative of the content of the polyatomic complexes in the silicon sample,
wherein optionally the second determination unit is configured to choose the calibration curve depending on an oxygen content in the silicon sample to be analyzed.

* * * * *